US00PP34465P2

(12) United States Plant Patent
Mazzardis

(10) Patent No.: US PP34,465 P2
(45) Date of Patent: Aug. 2, 2022

(54) BLUEBERRY PLANT NAMED 'NS 15-14'

(50) Latin Name: ***Vaccinium* hybrid**
Varietal Denomination: 'NS 15-14'

(71) Applicant: Next Progeny Pty., Ltd., Subiaco (AU)

(72) Inventor: Vincent David Andrew Mazzardis, Joondalup (AU)

(73) Assignee: Next Progeny Pty., Ltd., Subiaco (AU)

( * ) Notice: Subject to any disclaimer, the term of this patent is extended or adjusted under 35 U.S.C. 154(b) by 0 days.

(21) Appl. No.: 17/487,468

(22) Filed: Sep. 28, 2021

(30) Foreign Application Priority Data

Mar. 9, 2021 (QZ) ..... PBR 2021/0699

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

(56) References Cited

U.S. PATENT DOCUMENTS

PP25,858 P3 9/2015 Mazzardis
PP25,859 P3 9/2015 Mazzardis
PP25,860 P3 9/2015 Mazzardis
PP25,889 P3 9/2015 Mazzardis
PP26,172 P3 12/2015 Mazzardis
PP26,173 P3 12/2015 Mazzardis
PP27,142 P3 9/2016 Mazzardis
PP28,149 P3 7/2017 Mazzardis
PP28,217 P3 7/2017 Mazzardis
PP28,334 P3 8/2017 Mazzardis
PP28,357 P3 9/2017 Mazzardis
PP28,358 P3 9/2017 Mazzardis
PP30,626 P3 7/2019 Mazzardis
PP30,755 P3 7/2019 Mazzardis
PP30,756 P3 7/2019 Mazzardis
PP30,846 P2 8/2019 Mazzardis
PP30,934 P3 10/2019 Mazzardis
PP32,745 P3 1/2021 Mazzardis
PP32,781 P3 2/2021 Mazzardis
PP32,823 P3 2/2021 Mazzardis
PP32,897 P3 3/2021 Mazzardis
PP33,087 P3 5/2021 Mazzardis
PP33,154 P3 5/2021 Mazzardis
PP33,112 P3 6/2021 Mazzardis
PP33,137 P3 6/2021 Mazzardis
PP33,138 P3 6/2021 Mazzardis
PP33,384 P3 8/2021 Mazzardis
PP33,494 P3 9/2021 Mazzardis

OTHER PUBLICATIONS

Mazzardis, U.S. Appl. No. 17/336,801, filed Jun. 2, 2021.

*Primary Examiner* — Keith O. Robinson
(74) *Attorney, Agent, or Firm* — Randall Danskin, P.S.

(57) ABSTRACT

A new and distinct variety of blueberry plant, which is denominated varietally as 'NS 15-14' is described, with an upright plant growth habit and which produces fruit considered very large in size, medium in firmness, and low in acidity under the ecological conditions prevailing in Yanchep, Western Australia.

2 Drawing Sheets

Latin name: *Vaccinium* hybrid.

Variety denomination: The invention relates to a new, novel, and distinct variety of blueberry plant, a *Vaccinium* hybrid, with a variety denomination hereinafter as 'NS 15-14'.

CROSS REFERENCE TO RELATED APPLICATIONS

This application claims the benefit of priority under 35 USC § 119 to Community Plant Variety Office (CPVO) Application No. 2021/0699 for Community Plant Variety Rights, filed on Mar. 9, 2021 for a blueberry plant with a variety denomination of 'NS 15 14', which is herein incorporated by reference in its entirety.

SUMMARY

The new variety of blueberry plant resulted from an ongoing development program of plant breeding conducted to identify such plants. The purpose of the program was to improve the commercial quality of blueberry plants and other plant species. To this end, controlled, hybrid, cross-pollinations were made in order to produce plant populations from which improved progeny were evaluated and thereafter selected.

The 'NS 15-14' blueberry plant was originated and selected from a population of new plants growing on the breeder's property, which is located at Yanchep Springs in Yanchep, Western Australia. The new variety of blueberry plant was derived from a controlled, hybrid, cross-pollination of the seed parent, blueberry plant 'EB 9-4' (U.S. Plant Pat. No. 28,334), and a pollen parent, blueberry plant 'EB 8-50' (U.S. Plant Pat. No. 28,357) during the 2013 growing season.

Prior Varieties. The seed parent 'EB 9-4' is characterized principally by a semi-upright to intermediate growth habit, a medium vigor, a very early season first pick date, and further produces large- to very-large-sized, firm, high sweetness, and low to medium acidity fruit under the ecological conditions occurring in Yanchep, Western Australia. Also, the seed parent 'EB 9-4' exhibits a very early date of bloom time, a medium fruit cluster density, and a last pick date in February of the following year under the ecological conditions occurring in Yanchep, Western Australia. Further, the seed parent 'EB 9-4' is evergreen and produces fruit on one-year-old and current season's shoots.

The pollen parent 'EB 8-50', on the other hand, is characterized principally by a semi-upright to intermediate growth habit, a medium vigor, a very early season first pick date, and further produces large- to very-large-sized, firm to very firm, high to very high sweetness, and low acidity fruit under the ecological conditions occurring in Yanchep, Western Australia. Also, the pollen parent 'EB 8-50' exhibits a very early date of bloom time, a dense fruit cluster density, and a December last pick date under the ecological conditions occurring in Yanchep, Western Australia. Further, the pollen parent 'EB 8-50' is evergreen and produces fruit on one-year-old and current season's shoots.

Origin. The seed from the seed parent 'EB 9-4' produced approximately 1,100 plants following cross-pollination. These new plants were then grown at the aforementioned property, and fruit from these new plants was first observed in 2015. A subsequent assessment of these same self-fertile, new plants conducted during the 2015 growing season led to selecting the 'NS 15-14' variety for additional evaluation in 2018, which led to selection for further evaluation.

Asexual Reproduction. The further evaluation included an asexual vegetative propagation, by vegetative cuttings, at Yanchep Springs in Yanchep, Western Australia. Subsequent evaluations of the newly derived plants in the 2018 growing season led to a conclusion that the 'NS 15-14' variety was a distinct and new variety of blueberry plant found to be true to the original plant. The new variety of blueberry plant was considered to be novel in view of its upright growth habit, very large fruit size, medium firm fruit, and low fruit acidity.

Comparisons. In comparison to the seed parent 'EB 9-4' under the ecological conditions occurring in Yanchep, Western Australia, the new variety is noteworthy. In this regard, the seed parent has a plant growth habit considered to be semi-upright to intermediate. In contrast, the new variety of blueberry plant has a plant growth habit considered to be upright. In addition, the seed parent produces fruit with a size considered to be large to very large. This is in contrast to the fruit of the new variety of blueberry plant, which is considered to be very large in size. Also, the seed parent produces fruit considered to be firm. This is in contrast to the fruit of the new variety of blueberry plant, which is considered to be medium in firmness. Further, the seed parent produces fruit considered to be low to medium in acidity. This is in contrast to the fruit of the new variety of blueberry plant, which is considered to be low in acidity.

In comparison to the pollen parent 'EB 8-50' under the ecological conditions occurring in Yanchep, Western Australia, the new variety is noteworthy. In this regard, the pollen parent has a plant growth habit considered to be semi-upright to intermediate. In contrast, the new variety of blueberry plant has a plant growth habit considered to be upright. In addition, the pollen parent produces fruit with a size considered to be large to very large. This is in contrast to the fruit of the new variety of blueberry plant, which is considered to be very large in size. Also, the pollen parent produces fruit considered to be firm to very firm. This is in contrast to the fruit of the new variety of blueberry plant, which is considered to be medium in firmness. Further, the pollen parent and the new variety of blueberry plant both produce fruit considered to be low in acidity.

The new variety of blueberry plant is readily distinguishable from the most closely related, known variety, the 'EB 9-4' pollen parent.

The comparisons described above are summarized in Table 1 below.

TABLE 1

Summary of Comparisons

| | 'NS 15-14' | 'EB 9-4' (Seed) | 'EB 8-50' (Pollen) |
|---|---|---|---|
| Plant growth habit | Upright | Semi-upright to intermediate | Semi-upright to intermediate |
| Fruit size | Very large | Large to very large | Large to very large |
| Fruit firmness | Medium | Firm | Firm to very firm |
| Fruit acidity | Low | Low to medium | Low |

In addition, Table 2 below compares the 'NS 15-14' variety to sibling cultivars that resulted from the same seed parent 'EB 9-4' and pollen parent 'EB 8-50', namely, 'NS 16-2' (U.S. Plant Pat. No. 32,897), 'NS 16-18' (U.S. Plant Pat. No. 33,494), and 'NS 15-15' (U.S. Plant application Ser. No. 17/497,321).

TABLE 2

Comparison to Sibling Cultivars

| | 'NS 15-14' | 'NS 16-2' | 'NS 16-18' | 'NS 15-15' |
|---|---|---|---|---|
| Plant growth habit | Upright | Semi-upright | Upright | Upright |
| Fruit size | Very large | Very large | Large to very large | Very large |
| Fruit firmness | Medium | Very firm | Firm to very firm | Firm |
| Fruit acidity | Low | Low | Medium to high | Low to medium |
| Plant vigor | Weak to medium | Medium | Weak to medium | Medium |
| Fruit sweetness | Medium to high | Medium to high | Medium | Medium to high |

BRIEF DESCRIPTION OF THE DRAWINGS

The accompanying drawings are color photographs of the new blueberry plant 'NS 15-14' during the third year of growth under the ecological conditions prevailing at the breeder's property, which is located at Yanchep Springs in Yanchep, Western Australia.

Figure 1:
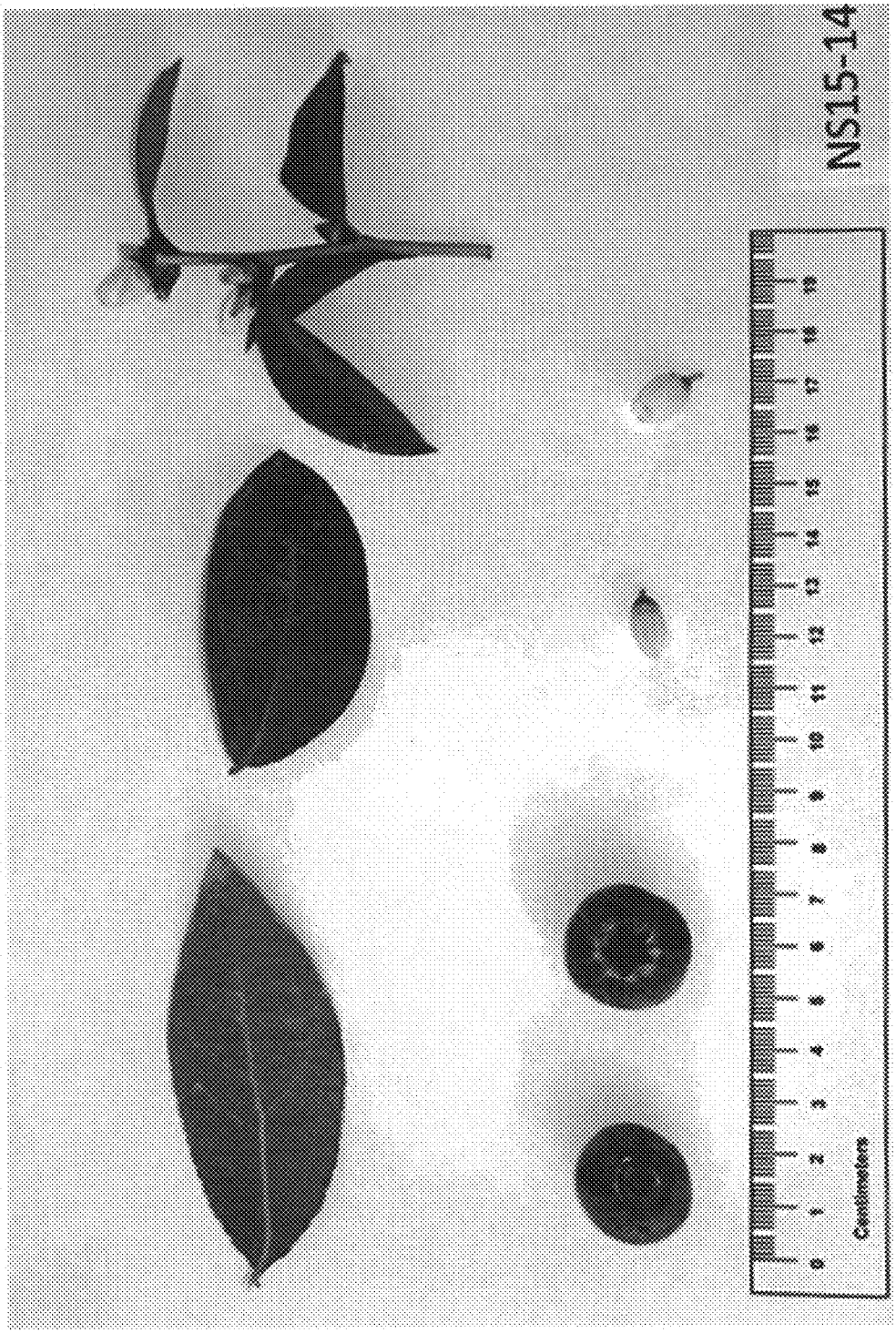
FIG. 1 is a color photograph, which shows fruit, blooms, leaves, and a portion of a vegetative stem of the new blueberry plant 'NS 15-14', the fruit being sufficiently mature for harvesting and shipment. This photograph also depicts the fruit size and the color of the ripe fruit, two leaves showing the sizes and the upper and under side colorations thereof, two blooms at different stages of maturation, and additional leaves on the stem at different stages of maturation.
Figure 2:
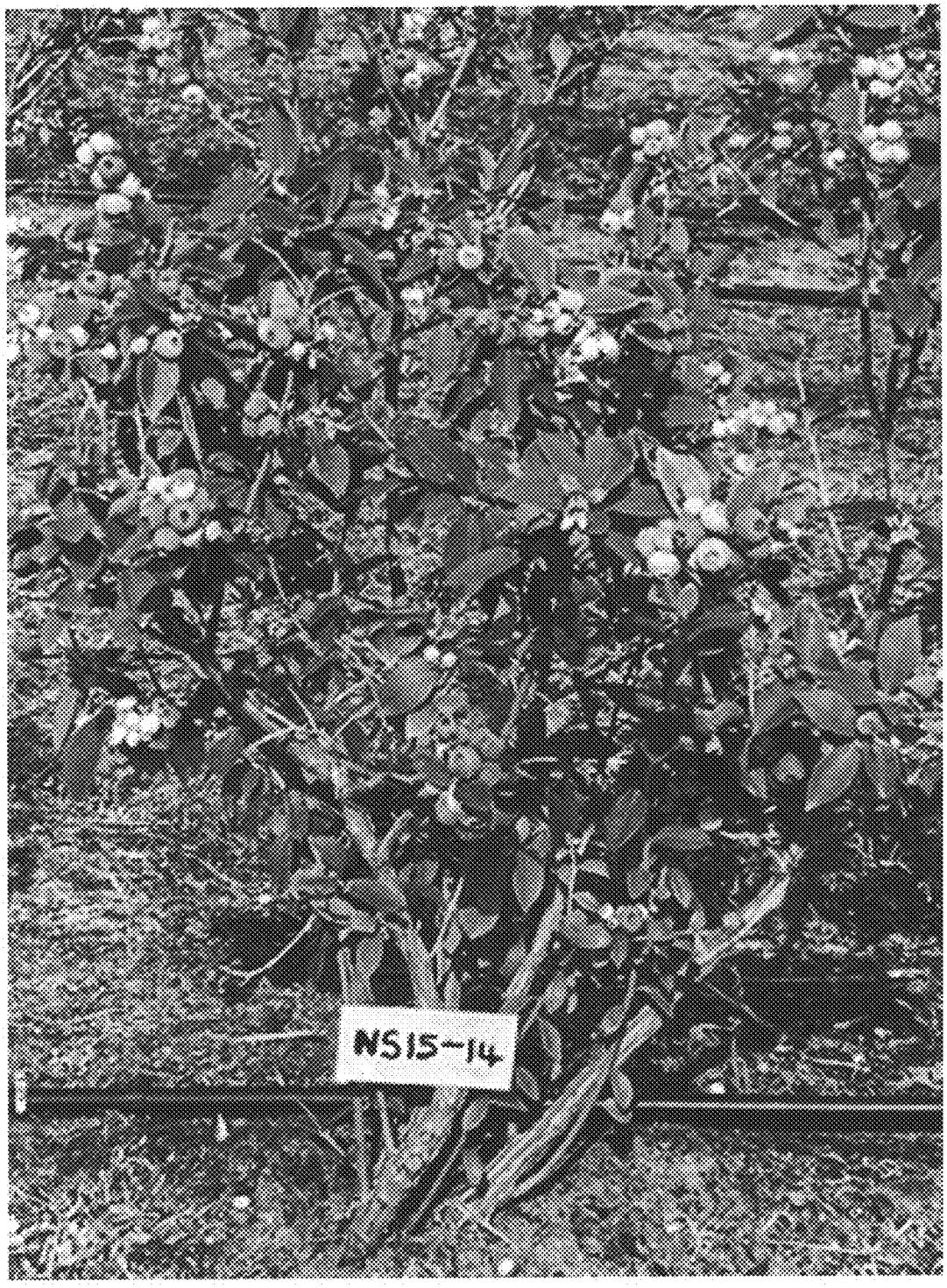
FIG. 2 is a color photograph, which shows the new blueberry plant 'NS 15-14.' This photograph depicts a mature bush with ripe and unripe fruits, the fruit size, and the upright growth habit of the bush. The ripe fruit is sufficiently mature for harvesting and shipment.

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Sixth Edition (2015), hereinafter, "RHS") and descriptions provided.

DETAILED BOTANICAL DESCRIPTION

Not a Commercial Warranty. The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of blueberry plant, the following has been observed during the third year of growth under the ecological conditions prevailing at the breeder's property, which is located at Yanchep Springs in Yanchep, Western Australia.

Plant: General.

*Vigor.*—Considered weak to medium for the species.

*Growth habit.*—Considered upright, in like manner to the commercial variety 'Ivanhoe' (unpatented). This is in contrast to the seed parent 'EB 9-4' (also the closest known variety) and the pollen parent 'EB 8-50', wherein the growth habit is considered to be semi-upright to intermediate.

*Average size of plant.*—1.15 meters in height by 0.70 meters in width.

*Internode length (space between nodes).*—Considered short to medium, 14.43 millimeters (mm).

*Bark color.*—RHS Greyish Red Orange Group 177D.

*Color, one year old shoots.*—RHS Greyed Orange Group 173A.

*Fruiting type.*—On one-year-old shoots and current season's shoots, in like manner to commercial varieties 'Concord' (unpatented) and 'Burlington' (unpatented).

Foliage: General.

*Average leaf length.*—Considered medium to long for the species, 61.45 mm.

*Average leaf width.*—Considered medium for the species, 27.03 mm.

*Color of leaf upper.*—RHS Darkish Yellow Green Group 139A.

*Color of leaf underside.*—RHS Moderate Yellow Green Group 138B.

*Vein color of plant leaf.*—RHS Light Yellow Green Group 144D.

*Venation pattern of leaf.*—Pinnate reticulate.

*Leaf apex texture.*—Glabrous.

*Leaf apex shape.*—Acute.

*Leaf base shape.*—Acute.

*Leaf shape.*—Elliptic.

*Leaf margin.*—Serrate.

*Leaf arrangement of plant.*—Alternate.

*Petiole length.*—3.21 mm.

*Petiole diameter.*—2.2 mm.

*Petiole color.*—RHS Strong Yellow Green 144C.

Flowers:

*Number of flowers/inflorescence.*—4-6.

*Length of inflorescence (excluding pedicel).*—Considered long, 10.21 mm.

*Corolla shape.*—Urceolate.

*Corolla tube surface texture.*—Ridges are present on the corolla tube.

*Average corolla length.*—12.57 mm.

*Corolla diameter.*—8.90 mm.

*Corolla aperture size.*—3.52 mm.

*Corolla color.*—RHS White Group NN155C.

*Pedicel color.*—RHS Light Yellow Green Group 145C.

*Pedicel length.*—4.01 mm.

*Average calyx diameter.*—Considered small, 3.53 mm.

*Average calyx basin depth.*—Considered medium, 1.98 mm.

*Attitude of sepals.*—Semi-erect.

*Type of sepals.*—Straight.

Reproductive organs:

*Size of pollen anthers.*—5.48 mm.

*Color of pollen anthers.*—RHS Greyed Orange Group 165B.

*Pistil length.*—7.39 mm.

*Pistil color.*—RHS Light Yellow Green Group 144D.

Fruit:

*Color of unripe fruit.*—RHS Strong Yellow Green Group 144B.

*Color of fruit skin.*—RHS Bluish Black Group 203C, also considered "dark blue" in like color to the commercial variety 'Heerma' (unpatented), after removal of bloom.

*Color of ripe fruit flesh.*—RHS Light Yellow Green Group 145D.

*Color of seeds.*—RHS Brownish Orange Group N167B.

*Average fruit size.*—Very large, 21-22 mm in diameter and 14.91 mm in height. This is in contrast to the seed parent 'EB 9-4' (also the closest known variety) and the pollen parent 'EB 8-50', wherein the fruit size is considered large to very large.

*Average weight of fruit.*—4 grams.

*Berry shape.*—Considered oblate.

*Sweetness when ripe.*—Considered medium to high for the species.

*Firmness when ripe.*—Considered medium for the species. This is in contrast to the seed parent 'EB 9-4' (the closest known variety), wherein the fruit firmness is considered firm. This is also in contrast to the pollen parent 'EB 8-50', wherein the fruit firmness is considered firm to very firm.

*Acidity when ripe.*—Considered low for the species. This is comparable to the pollen parent 'EB 8-50', wherein the fruit acidity is also considered low. This is in contrast to the seed parent 'EB 9-4' (the closest known variety), wherein the fruit acidity is considered low to medium.

*Cluster density.*—Considered medium for the species.

*Average fruit production.*—2-3 kilograms on a two-year-old bush.

*Storability of fruit.*—Considered excellent for the species.

*Market use of fruit.*—1st grade fresh market fruit.

*Date of vegetative bud burst.*—This variety is evergreen under the ecological conditions prevailing in Yanchep, Western Australia, but a vegetative bud break occurs in August, which is considered medium.

*Date of bloom time.*—This variety is evergreen under the ecological conditions prevailing in Yanchep, Western Australia, but a bloom time occurs on flowering first year shoots at April/May, which is considered very early on one-year-old shoots in like manner to the commercial variety 'Patriot' (unpatented) and is considered very early on current year's shoots.

*Duration of bloom time and bloom intensity.*—4-6 weeks; bloom intensity is considered strong.

*Beginning of fruit ripening.*—Considered very early on one-year-old shoot in like manner to the commercial variety 'Bluetta' (unpatented) and very early on current year's shoots.

*First pick date.*—The observed date of the first pick is approximately July under the ecological conditions prevailing in Yanchep, Western Australia.

*Last pick date.*—The observed date of the last pick is approximately September under the ecological conditions prevailing in Yanchep, Western Australia.

*Pollination requirements.*—Self-fertile.

*Resistance to pests and disease.*—No particular resistance noted. The variety has not been tested to detect any resistance.

Although the new variety of blueberry plant possesses the described characteristics when grown under the ecological conditions prevailing in Yanchep, Western Australia, it should be understood that variations are to be expected in the usual magnitude and characteristics incident to changes in growing conditions, fertilization, pruning, pest control, frost, climatic variables, and horticultural management.

Having thus described and illustrated a new variety of blueberry plant, what is claimed to secure a Plant Letters Patent is:

1. A new and distinct variety of blueberry plant named NS '15-14', substantially as illustrated and described, which is characterized principally as to novelty by an upright plant growth habit and by producing fruit considered very large in size, medium in firmness, and low in acidity under the ecological conditions prevailing in Yanchep, Western Australia.

* * * * *